United States Patent
Yu et al.

(10) Patent No.: US 9,981,050 B2
(45) Date of Patent: May 29, 2018

(54) BISPECIFIC PEPTIDE CONJUGATE AND RADIOACTIVE BISPECIFIC PEPTIDE IMAGING AGENT

(71) Applicant: Institute of Nuclear Energy Research, Atomic Energy Council, Executive Yuan, R.O.C., Taoyuan (TW)

(72) Inventors: Hung-Man Yu, Taoyuan (TW); Jyun-Hong Chen, Taoyuan (TW); Kun-Liang Lin, Taoyuan (TW); Chien-Jen Chen, Taoyuan (TW); Wuu-Jyh Lin, Taoyuan (TW)

(73) Assignee: INSTITUTE OF NUCLEAR ENERGY RESEARCH, ATOMIC ENERGY COUNCIL, EXECUTIVE YUAN, R.O.C., Taoyuan (TW)

( * ) Notice: Subject to any disclaimer, the term of this patent is extended or adjusted under 35 U.S.C. 154(b) by 0 days. days.

(21) Appl. No.: 15/157,905

(22) Filed: May 18, 2016

(65) Prior Publication Data

US 2017/0095581 A1  Apr. 6, 2017

(30) Foreign Application Priority Data

Oct. 6, 2015 (TW) .............................. 104132862 A

(51) Int. Cl.
| | | |
|---|---|---|
| A61K 38/00 | (2006.01) | |
| A61K 51/08 | (2006.01) | |
| C07K 7/08 | (2006.01) | |
| C07K 5/09 | (2006.01) | |

(52) U.S. Cl.
CPC .......... A61K 51/082 (2013.01); C07K 5/0817 (2013.01); C07K 7/08 (2013.01); C07K 2319/33 (2013.01)

(58) Field of Classification Search
CPC ...... A61K 51/082; C07K 5/0817; C07K 7/08; C07K 2319/33
See application file for complete search history.

(56) References Cited

PUBLICATIONS

Cardo-Vila et al. "From combinatorial peptide selection to drug prototype (II): Targeting the epidermal growth factor receptor pathway" Proc. Natl. Acad. Sci. 107:5118-5123. Published Mar. 16, 2010.*
Han et al. "A novel small peptide as an epidermal growth factor receptor targeting ligand for nanodelivery in vitro" Intl. J. Nanomedicine 8:1541-1549. Published Apr. 18, 2013.*
Yu et al. "Synthesis of 68Ga-labeled NOTA-RGD-GE11 heterodimeric peptide for dual integrin and epidermal growth factor receptor-targeted tumor imaging" J. Labelled Comp. and Radiopharm. 58:299-303. Published May 21, 2015.*
Guardiola et al. "Peptides Targeting EGF Block the EGF-EGFR Interaction" ChemBioChem 17:702-711. Published Jan. 25, 2016.*
Li et al. "Identification and characterization of a novel peptide ligand of epidermal growth factor receptor for targeted delivery of therapeutics". FASEB J. 19:1978-1985. (Year: 2005).*
Durkan et al. "A heterodimeric [RGD-Glu-[64Cu-NO2A]-6-Ahx-RM2]avb3/GRPr-targeting antagonist radiotracer for PET imaging of prostate tumors" Nuclear Medicine and Biology 41:133-139. (Year: 2014).*
Johnson et al. "64Cu-NO2A-RGD-Glu-6-Ahx-BBN(7-14)NH2: a heterodimeric targeting vector for positron emission tomography imaging of prostate cancer" Nucler Medicine and Biology 39:377-387. (Year: 2012).*
Hung-Man Yu et al., Synthesis of 68Ga-labeled NOTA-RGD-GE11 heterodimeric peptide for dual integrin and epidermal growth factor receptor-targeted tumor imaging, J. Label Compd. Radiopharm, 2015, 299-303, 58.

* cited by examiner

*Primary Examiner* — Christina Bradley
*Assistant Examiner* — Zachary J Miknis
(74) *Attorney, Agent, or Firm* — Locke Lord LLP; Tim Tingkang Xia, Esq.

(57) ABSTRACT

Disclosed herein is a bispecific peptide conjugate comprising an epidermal growth factor receptor (EGFR) targeting peptide, an αvβ3 integrin targeting peptide, and a linker, where the linker is conjugated respectively to the EGFR targeting peptide and the αvβ3 integrin targeting peptide.

5 Claims, 6 Drawing Sheets

BISPECIFIC PEPTIDE CONJUGATE AND RADIOACTIVE BISPECIFIC PEPTIDE IMAGING AGENT

CROSS-REFERENCE TO RELATED APPLICATION

This application also claims priority to Taiwan Patent Application No. 104132862 filed in the Taiwan Patent Office on Oct. 6, 2015, the entire content of which is incorporated herein by reference.

BACKGROUND OF THE INVENTION

In the last decade, tumor specific peptides receive great attentions, and great efforts are devoted to relevant research, such that the tumor specific peptides become a promising imaging agent and therapeutic agent for tumors. However, the existing tumor specific peptide is a monospecific peptide for tumors, which suffers from some problems and disadvantages during practical use, including (1) lower specific binding to tumor than that of antibody-based therapeutics; (2) short retention time in organisms, and undesirable pharmacokinetic properties; (3) large change and uncertainty of biomarkers and receptors on the tumor cells occurring during the development of tumor cells, thus causing undesirable imaging effect.

In view of this, there is an urgent need in the art for an improved specific peptide, to overcome the defects in the prior art.

SUMMARY

To make the essential meanings of the disclosure comprehensible to the reader, the summary provides the brief description of the disclosure. However, the summary is not elaboration of the disclosure, and not intended to define the technical features and the scope of the claims of the present invention.

To solve the above problems, this disclosure provides a bispecific peptide conjugate, which can simultaneously specifically bind to two different biomarkers or receptors, to improve the binding and pharmacokinetic properties of a conventional monospecific peptide for tumors.

The bispecific peptide conjugate of this disclosure comprises an epidermal growth factor receptor (EGFR) targeting peptide, an $\alpha_v\beta_3$ integrin targeting peptide, and a linker. The linker is conjugated respectively to the EGFR targeting peptide and the $\alpha_v\beta_3$ integrin targeting peptide.

According to an embodiment of this disclosure, the linker is cysteine-6-aminohexanoic acid.

According to another embodiment of this disclosure, the EGFR targeting peptide is a GE11 peptide having an amino acid sequence of YHWYGYTPQNVI (SEQ ID NO: 1).

According to another embodiment of this disclosure, the $\alpha_v\beta_3$ integrin targeting peptide is an RGD peptide having an amino acid sequence of RGD.

In an embodiment, the bispecific peptide conjugate further comprises a chelating group conjugated to the linker. In a specific embodiment, the chelating group is 1,4,7-triazacyclononane-N,N',N"-triacetic acid.

In a non-limiting embodiment, the bispecific peptide conjugate further comprises a radioactive isotope tagged on the chelating group. According to an optional embodiment, the radioactive isotope is Gallium-68, Copper-64, or Fluorine-18.

Another aspect of the present invention relates to a radioactive bispecific peptide imaging agent. The imaging agent comprises a bispecific peptide conjugate in an amount effective for imaging and an excipient useful in the imaging agent. Specifically, the bispecific peptide conjugate in an amount effective for imaging comprises an epidermal growth factor receptor (EGFR) targeting peptide, an $\alpha_v\beta_3$ integrin targeting peptide, a chelating group, a radioactive isotope tagged on the chelating group, and a linker which is conjugated respectively to the EGFR targeting peptide, the $\alpha_v\beta_3$ integrin targeting peptide, and the chelating group.

According to an embodiment of this disclosure, the linker is cysteine-6-aminohexanoic acid.

According to another embodiment of this disclosure, the EGFR targeting peptide is a GE11 peptide having an amino acid sequence of YHWYGYTPQNVI (SEQ ID NO: 1).

According to another embodiment of this disclosure, the $\alpha_v\beta_3$ integrin targeting peptide is an RGD peptide having an amino acid sequence of RGD.

In an embodiment, the bispecific peptide conjugate further comprises a chelating group conjugated to the linker. In a specific embodiment, the chelating group is 1,4,7-triazacyclononane-N,N',N"-triacetic acid.

In a non-limiting embodiment, the bispecific peptide conjugate further comprises a radioactive isotope tagged on the chelating group. According to an optional embodiment, the radioactive isotope is Gallium-68, Copper-64, or Fluorine-18.

The central concept and the employed technical means and various embodiments of the present invention may be fully understood by those of ordinary skill in the art upon reading the detailed description of the present invention.

BRIEF DESCRIPTION OF DRAWINGS

To make the above and other objectives, features, advantages, and examples of the present invention more comprehensible, the drawings are illustrated below, in which.

DETAILED DESCRIPTION OF DISCLOSED EMBODIMENTS

Figure 1:
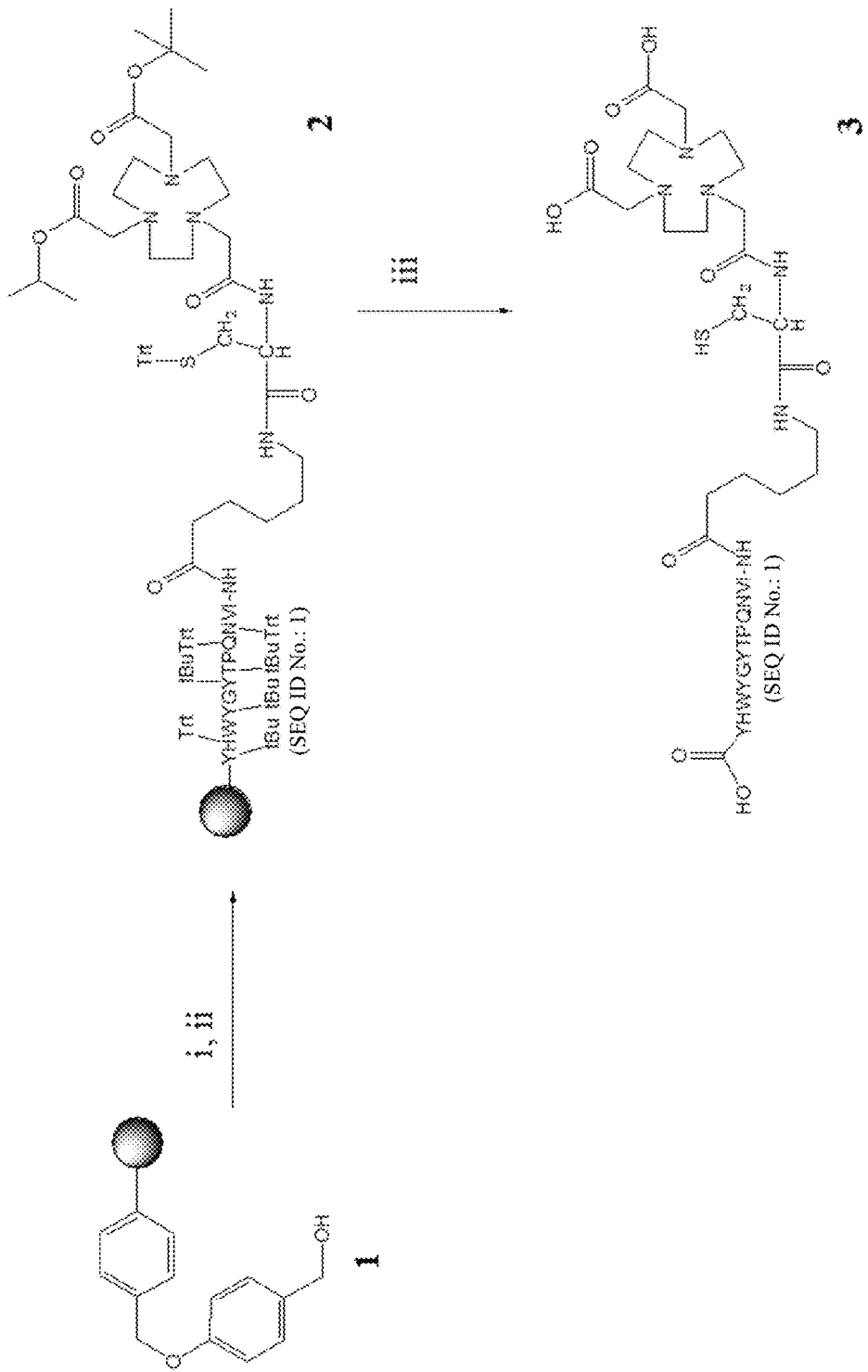
FIG. 1 is a flow chart for synthesizing a NOTA-cys-6-ahx-GE11 conjugate according to an embodiment of the present invention.

To make the description of the disclosure more thorough and complete, the implementations and specific examples of the present invention are described below, which however, are not exhaustive.

Unless stated otherwise, the scientific and technical terms used herein have the same meanings as commonly understood and used by one of ordinary skill in the art to which this invention belongs. Furthermore, the noun used herein embraces both the singular and plural forms of the referents, unless indicated otherwise.

As used herein, the term "about" generally refers to that the actual value is within 10%, 5%, 1%, or 0.5% of a particular value or range. The term "about" means herein that the actual value is within an acceptable standard error of the mean, depending on the considerations of those ordinary skill in the art to which this invention belongs. Besides the experimental examples, or unless stated specifically otherwise, it should be understood that the ranges, amounts, numerical values, and percentages used herein are modified by "about". Therefore, unless stated otherwise, the numerical values or parameters disclosed in the specification and claims are all rough values and may be varied as desired.

In the development of tumors and cancers, generally more than one biomarker or receptor is overexpressed. To solve the disadvantages of specific peptides existing in the prior art, the present inventors initially proposes a novel bispecific peptide conjugate, and a novel radioactive bispecific peptide imaging agent comprising the conjugate. The bispecific peptide conjugate of the present invention has the advantages of high affinity, sensitivity, and specificity for the targets in the tumor cells, and has desirable chemical and pharmacokinetic properties in organisms. Moreover, the radioactive bispecific peptide imaging agent comprising the conjugate provided in the present invention further has other advantages. For example, the radiolabelling procedure for the imaging agent is much simple and rapid, and the precursor of the imaging agent can be produced and supplied simply and quickly, which facilitate the reduction of the cost and the promoting and marketing.

Specifically, the bispecific peptide conjugate of the present invention mainly comprises, in structure, peptides specifically binding respectively to the epidermal growth factor receptor (EGFR) and the $\alpha_v\beta_3$ integrin, in which the two peptides are a GE11 peptide having an amino acid sequence of YHWYGYTPQNVI (SEQ ID NO: 1); and an RGD peptide having an amino acid sequence of RGD.

EGFR is overexpressed in a variety of cancers. For example, EGFR is overexpressed in 60 to 90% of non-small lung cell cancers (NSCLC). Moreover, the integrin $\alpha_v\beta_3$, as a marker of neoangiogenesis, is overexpressed in tumor cells and newly generated peripheral vessels in many cancers. Therefore, in order to increase the sensitivity and specificity of the specific peptide for targets in the cancer cells, the bispecific peptide conjugate of the present invention can simultaneously recognize and specifically bind to EGFR and $\alpha_v\beta_3$ integrin, two different biomarkers.

Furthermore, in a non-limiting embodiment, the bispecific peptide conjugate of the present invention further comprises a linker, in addition to the two peptides (that is, GE11 and RGD peptide) able to recognize two different targets. The linker functions to maintain a suitable distance between two different specific peptides, or between the peptide and the chelating group, to reduce the occurrence of interference with each other. Moreover, the linker may also be arranged to change and adjust the in-vivo pharmacokinetic properties of the bispecific peptide conjugate of the present invention. In a specific embodiment, the linker is cysteine-6-aminohexanoic acid.

Moreover, the bispecific peptide conjugate of the present invention may further comprise a chelating group, which functions to allow the bispecific peptide conjugate to be tagged with a suitable radioactive isotope. In an optional embodiment, the radioactive isotope is Gallium-68, Copper-64, or Fluorine-18. According to a specific embodiment of this disclosure, the chelating group is 1,4,7-triazacyclononane-N,N',N"-triacetic acid (NOTA).

The radioactive bispecific peptide imaging agent comprises a bispecific peptide conjugate in an amount effective for imaging and an excipient useful in the imaging agent. The amount effective for imaging may be adjusted according to the physiological conditions and status of the subjects intended for being imaged, for example, the course of disease, gender, or body weight of the patients. The amount effective for imaging may be decided by those of ordinary skill in the art based on their general knowledge according to the situation in practical use.

Examples are given below to illustrate various implementations of the present invention, such that the technical solutions disclosed herein may be practiced by one of ordinary skill in the art to which this invention belongs based on the description in the specification. Accordingly, the examples given below are not intended to limit the scope of the claims of the present invention. Moreover, the literatures cited herein are all deemed as being incorporated by reference as part of this specification.

EXAMPLE 1

Synthesis of Bispecific Peptide Conjugate

The bispecific peptide (that is, NOTA-c(RGDyk)-cys-6-ahx-GE11) used in the experimental example was prepared following the method described in Hung-Man Yu et al., J. Label Compd. Radiopharm 2015, 58 299-303. Briefly, NOTA-cys-6-ahx-GE11 was synthesized by using a peptide synthesizer, then purified by MPLC, and determined by MS to have a molecular weight of 1022.5 $[M+2H]^{2+}$. The preparation process of NOTA-cys-6-ahx-GE11 is as shown in FIG. 1.

Figure 2:
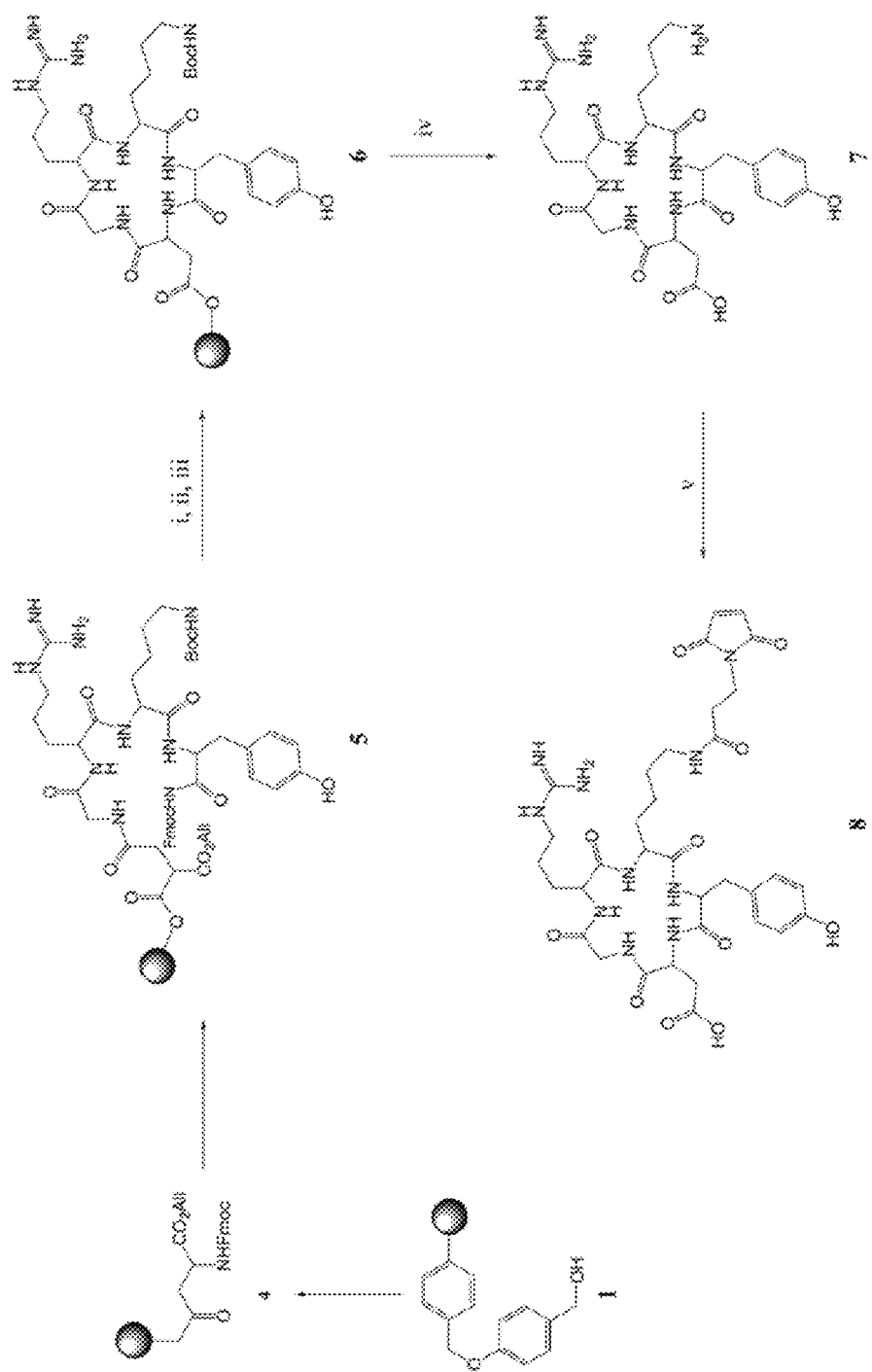
FIG. 2 is a flow chart for synthesizing a Maleimidopropyl-c(RGDyK) conjugate according to an embodiment of the present invention.

On the other hand, c(RGDyK) was synthesized by using a peptide synthesizer, then purified by MPLC, and determined by MS to have a molecular weight of 620.3 $[M+2H]^+$ (The preparation process is as shown in FIG. 2). Maleimidopropyl-c(RGDyK) was synthesized, purified by MPLC, and determined by MS to have a molecular weight of 771.8 $[M+2H]^+$. The preparation process of maleimidopropyl-c(RGDyK) is as shown in FIG. 2.

Figure 3:
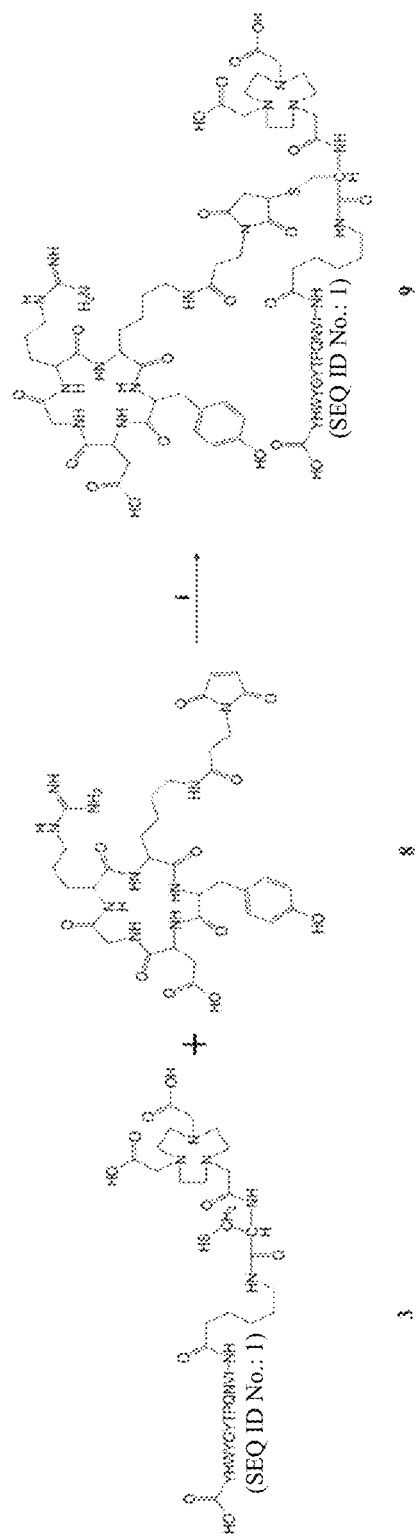
FIG. 3 is a flow chart for producing NOTA-c(RGDyk)-cys-6-ahx-GE11 (that is, the bispecific peptide conjugate of the present invention) by linking NOTA-cys-6-ahx-GE11 to maleimidopropyl-c(RGDyK)

The NOTA-cys-6-ahx-GE11 and maleimidopropyl-c(RGDyK) thus prepared were linked, to produce NOTA-c(RGDyk)-cys-6-ahx-GE11, which was purified by MPLC, and determined by MS to have a molecular weight of 1047.6 $[M+2H]^{2+}$. Final yield: 43%, chemical purity >95%. The preparation process of NOTA-c(RGDyk)-cys-6-ahx-GE11 is as shown in FIG. 3.

EXAMPLE 2

Figure 4:
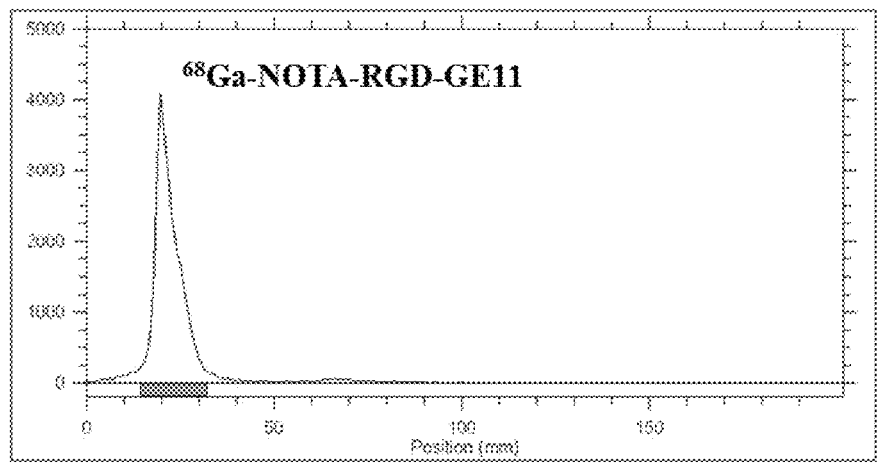
FIG. 4 is a radio-TLC scanning image of $^{68}$Ga-NOTA-RGD-GE11 according to an embodiment of the present invention.
Figure 5:
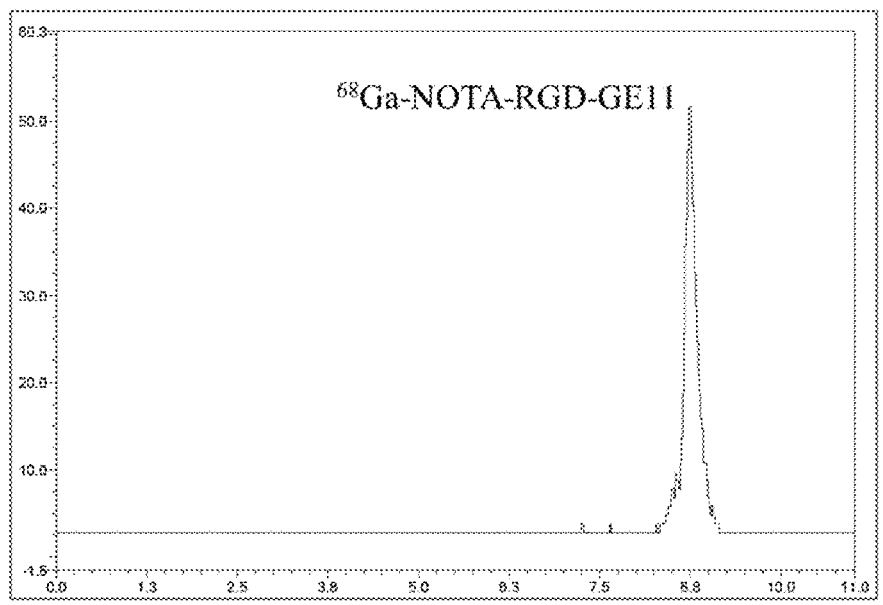
FIG. 5 is a radio-HPLC chromatogram of $^{68}$Ga-NOTA-RGD-GE11 according to an embodiment of the present invention.

Bispecific Peptide Conjugate Tagged with Radioactive $^{68}$Ga of the Present Invention In the experimental example, the bispecific peptide bearing a radioactive tag was prepared following the method described in Hung-Man Yu et al., J. Label Compd. Radiopharm 2015, 58 299-303. The preparation method was briefly described as follows. A $^{68}$Ge/$^{68}$Ga generator was panned with 0.1N HCl, to obtain a $^{68}$GaCl$_3$ solution. Then, 0.5 mL of $^{68}$Ga (~185 MBq) and 0.15 mL of 1M HEPES buffer were added to 5 μg NOTA-RGD-GE11, and reacted for 15 min at room temperature. The radiochemical purity (RCP) was determined by using radio-TLC and radio-HPLC. The results are respectively shown in FIGS. 4 and 5. The bispecific peptide conjugate ($^{68}$Ga-NOTA-RGD-GE11) tagged with radioactive $^{68}$Ga in this example has an RCP that is greater than 95%.

EXAMPLE 3

Specific Binding Assay of the Bispecific Peptide of the Present Invention for EGFR and αV Integrin (Alpha-V Integrin) in Tumor Cells In this example, the bispecific peptide conjugate (that is, NOTA-c(RGDyk)-cys-6-ahx-GE11) prepared in Example 1 was assayed.

A549 tumor cells were plated in a 96-well plate (5×10$^4$ cells/well). Various concentrations of NOTA-c(RGDyk)-cys-6-ahx-GE11 and anti-EGFR antibody or anti-integrin αV antibody were added and reacted for 2 hrs. Then, a secondary antibody and ABTS were added and reacted for 8 hrs. The antibody binding was assayed by a fluorimeter. The experimental results are shown in FIGS. 6A and 6B.

Figure 6B:
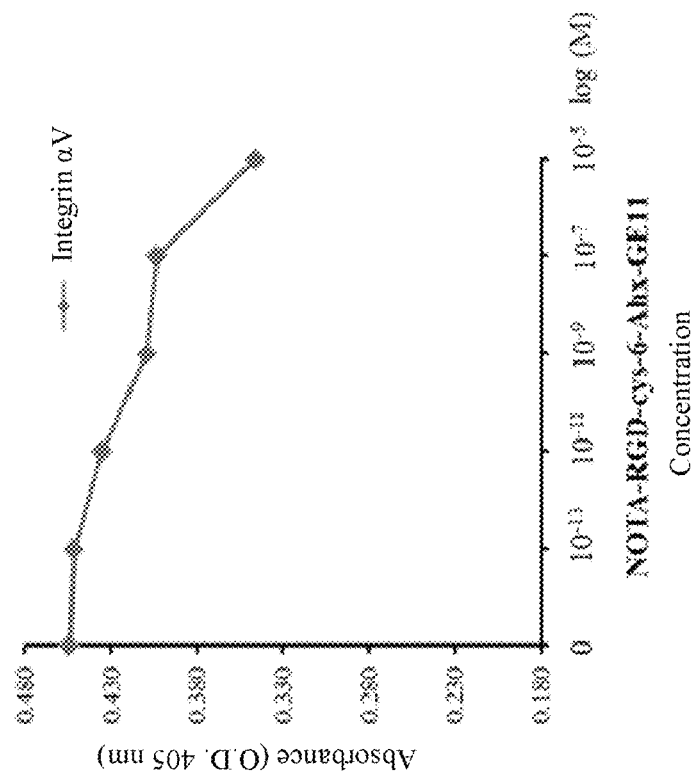
FIG. 6B shows test results of specific binding of NOTA-c(RGDyk)-cys-6-ahx-GE11 to integrin $\alpha$V in A549 tumor cells.
Figure 6A:
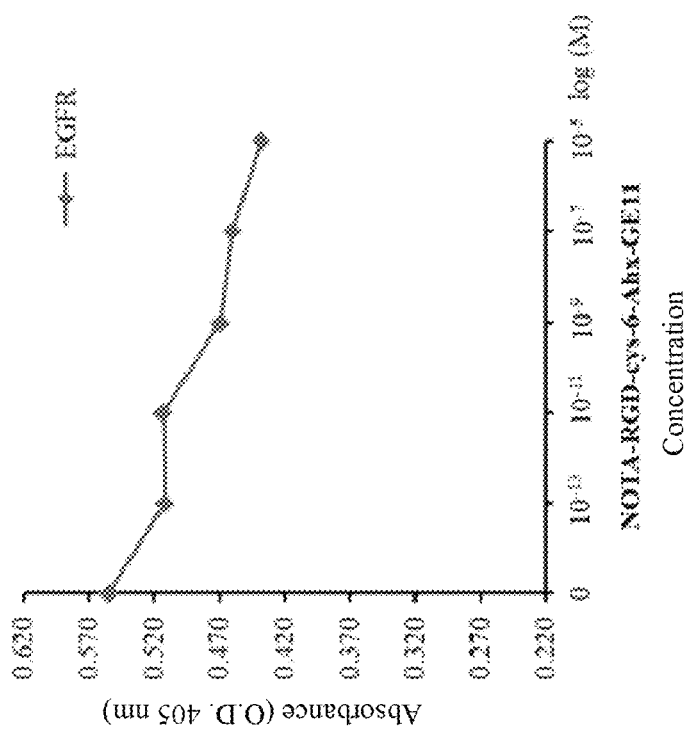
FIG. 6A shows results of specific binding assay of NOTA-c(RGDyk)-cys-6-ahx-GE11 to EGFR in A549 tumor cells.

Referring to FIGS. 6A and 6B, the specific peptide conjugate (that is, NOTA-c(RGDyk)-cys-6-ahx-GE11) of the present invention can effectively inhibit the binding of the anti-EGFR antibody and anti-integrin αV antibody to tumor cells, and the absorbance decreases with increasing concentrations of bispecific peptide of the present invention. The experimental results suggest that the bispecific peptide conjugate NOTA-c(RGDyk)-cys-6-ahx-GE11 of the present invention has the ability to specifically bind to EGFR and integrin αV.

EXAMPLE 4

Positron Emission Tomography/Computed Tomography (PET/CT) Imaging with the Bispecific and Monospecific Peptide Conjugates Tagged with a Radioactive Isotope of the Present Invention in Tumor Bearing Animals In this example, the bispecific peptide conjugate (that is, $^{68}$Ga-NOTA-RGD-GE11) tagged with a radioactive isotope prepared in Example 2 was tested and was compared with monospecific peptide conjugate $^{68}$Ga-NOTA-GE11.

Figures 7A, 7B:
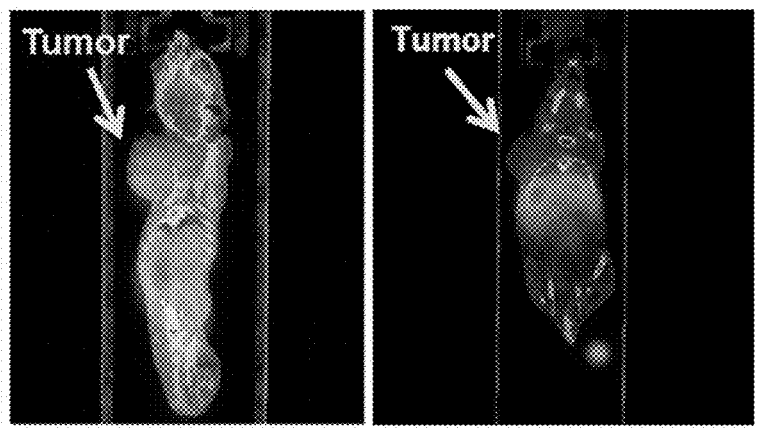
FIG. 7A is a Positron Emission Tomography (PET) image with $^{68}$Ga-NOTA-RGD-GE11 in a tumor bearing animal.
FIG. 7B is a Positron Emission Tomography (PET) image with $^{68}$Ga-NOTA-GE11 in a tumor bearing animal.

The right thigh of nude mice was subcutaneously inoculated with 5×10$^6$ NCI-H292 tumor cells. The tumors were allowed to grow for about 4 weeks until the tumor size reached 0.5 cm diameter. Then, the animals were anesthetized with isoflorane, injected with 11 MBq $^{68}$Ga-NOTA-RGD-GE11 or $^{68}$Ga-NOTA-GE11 (0.1 mL) via the tail vein, and imaged for 2 hours by Positron Emission Tomography/Computed Tomography (PET/CT). The obtained image is shown in FIG. 7A and FIG. 7B. The images were quantified by using PMODE Software. The result shows that the tumor/muscle ratio (T/M ratio) of $^{68}$Ga-NOTA-RGD-GE11 and $^{68}$Ga-NOTA-GE11 at 2 hours post-injection are 4.31 and 1.87 respectively.

It can be known from the results obtained in the above examples that the bispecific peptide conjugate tagged with a radioactive isotope disclosed herein is useful as a bispecific peptide imaging agent, for which a radioactive labeling method is established. Moreover, it is confirmed by the results from PET/CT that the bispecific peptide imaging agent of the present invention can facilitate the development of nuclear medicine imaging in tumor detection and in evaluation of therapy and prognosis.

The specific examples disclosed above are not intended to limit the scope of the claims of the present invention. Modifications may be made by those of ordinary skill in the art based on their general knowledge without departing from the principle and spirit of the present invention, and thus the scope of the present invention is defined by the claims.

---

---

What is claimed is:

1. A bispecific peptide conjugate, comprising:
    an epidermal growth factor receptor (EGFR) targeting peptide, wherein the EGFR targeting peptide is a GE11 peptide;
    an α$_v$β$_3$ integrin targeting peptide, wherein the αvβ$_3$ integrin targeting peptide is an RGD peptide; and
    a linker, conjugated respectively to the EGFR targeting peptide and the α$_v$β$_3$ integrin targeting peptide, wherein the linker is cysteine-6-aminohexanoic acid; and
    a chelating group conjugated to the linker, wherein the chelating group is 1,4,7-triazacyclononane-N,N',N''-triacetic acid.

2. The bispecific peptide conjugate according to claim 1, further comprising a radioactive isotope tagged on the chelating group.

3. The bispecific peptide conjugate according to claim 2, wherein the radioactive isotope is Gallium-68, Copper-64, or Fluorine-18.

4. A radioactive bispecific peptide imaging agent, comprising:
   a bispecific peptide conjugate in an amount effective for imaging, comprising:
   an epidermal growth factor receptor (EGFR) targeting peptide, wherein the EGFR targeting peptide is a GE11 peptide;
   an $\alpha_v\beta_3$ integrin targeting peptide, wherein the $\alpha v\beta 3$ integrin targeting peptide is an RGD peptide;
   a chelating group, wherein the chelating group is 1,4,7-triazacyclononane-N,N',N"-triacetic acid;
   a radioactive isotope tagged on the chelating group; and
   a linker, conjugated respectively to the EGFR targeting peptide, the $\alpha_v\beta_3$ integrin targeting peptide, and the chelating group, wherein the linker is cysteine-6-aminohexanoic acid; and
   an excipient useful in the imaging agent.

5. The radioactive bispecific peptide imaging agent according to claim 4, wherein the radioactive isotope is Gallium-68, Copper-64, or Fluorine-18.

* * * * *

SEQUENCE LISTING

```
<160> NUMBER OF SEQ ID NOS: 1

<210> SEQ ID NO 1
<211> LENGTH: 12
<212> TYPE: PRT
<213> ORGANISM: Artificial Sequence
<220> FEATURE:
<223> OTHER INFORMATION: GE11

<400> SEQUENCE: 1

Tyr His Trp Tyr Gly Tyr Thr Pro Gln Asn Val Ile
1               5                   10
```